(12) United States Patent
Jiang et al.

(10) Patent No.: US 9,662,282 B2
(45) Date of Patent: May 30, 2017

(54) METHOD FOR PREPARING ROUND EMULSION BEADS USING LOW TEMPERATURE COOLING AND THE PRODUCT THEREOF

(71) Applicant: KPT LTD, Chungcheongbuk-do (KR)

(72) Inventors: Yanfu Jiang, Yongin-si (KR); Ik Joo Lee, Ansan-si (KR); Woon Jang Lee, Cheongju-si (KR); Byung-Ho Park, Cheongju-si (KR); Jae Uk Lee, Daejeon (KR)

(73) Assignee: KPT LTD, Chungcheongbuk-Do (KR)

( * ) Notice: Subject to any disclaimer, the term of this patent is extended or adjusted under 35 U.S.C. 154(b) by 0 days.

(21) Appl. No.: 14/443,228

(22) PCT Filed: Mar. 28, 2013

(86) PCT No.: PCT/KR2013/002592
§ 371 (c)(1),
(2) Date: May 15, 2015

(87) PCT Pub. No.: WO2014/157752
PCT Pub. Date: Oct. 2, 2014

(65) Prior Publication Data
US 2015/0297474 A1    Oct. 22, 2015

(51) Int. Cl.
*A61J 3/00* (2006.01)
*A61K 8/06* (2006.01)
(Continued)

(52) U.S. Cl.
CPC ............... *A61K 8/064* (2013.01); *A61J 3/00* (2013.01); *A61K 8/0216* (2013.01); *A61K 8/06* (2013.01);
(Continued)

(58) Field of Classification Search
CPC ................ A61J 3/00; A61K 2800/412; A61K 2800/622; A61K 2800/624;
(Continued)

(56) References Cited

U.S. PATENT DOCUMENTS

| | | |
|---|---|---|
| 5,401,502 A | 3/1995 | Wunderlich et al. |
| 6,214,394 B1 | 4/2001 | Beer |

(Continued)

FOREIGN PATENT DOCUMENTS

| | | |
|---|---|---|
| KR | 20030029523 A | 4/2003 |
| KR | 20050091572 A | 9/2005 |

(Continued)

OTHER PUBLICATIONS

Quian et al. (Journal of Materials Chemistry 2009, 19, 3 pages).*

(Continued)

*Primary Examiner* — Ernst V Arnold
(74) *Attorney, Agent, or Firm* — Lucas & Mercanti, LLP

(57) ABSTRACT

The present invention relates to a method for manufacturing solid round emulsion beads by dropping liquid emulsion into a cryogenic freezing refrigerant. The obtained solid round emulsion beads can be stored and used at a low temperature. The solid round emulsion beads can be coated with a solution containing a composition which is solid at room temperature or which can form gel. The emulsion beads can be prepared by using liquid emulsion containing additional composition, which is solid at room temperature or can form gel, in the water phase of oil-in-water (O/W) emulsion or the oil phase of oil-in-water (W/O) emulsion. The emulsion beads prepared by the present invention can maintain its shape without swelling and/or damage but with stability and does not give any grainy feeling when the liquid emulsion was applied on the skin.

7 Claims, 3 Drawing Sheets

(51) Int. Cl.
    *F25D 31/00*     (2006.01)
    *A61Q 19/00*     (2006.01)
    *A61K 8/02*     (2006.01)

(52) U.S. Cl.
    CPC .............. *A61Q 19/00* (2013.01); *F25D 31/00* (2013.01); *A61K 2800/412* (2013.01); *A61K 2800/622* (2013.01); *A61K 2800/624* (2013.01); *A61K 2800/805* (2013.01)

(58) Field of Classification Search
    CPC .. A61K 2800/805; A61K 8/0216; A61K 8/06; A61K 8/064; A61Q 19/00; F25D 31/00
    See application file for complete search history.

(56) References Cited

U.S. PATENT DOCUMENTS

| 2006/0154067 | A1* | 7/2006 | Cooper | C08J 9/16 |
|---|---|---|---|---|
| | | | | 428/402 |
| 2008/0226721 | A1 | 9/2008 | Cooper et al. | |

FOREIGN PATENT DOCUMENTS

| WO | 90/13780 A1 | 11/1990 |
|---|---|---|
| WO | 03/049849 A2 | 6/2003 |
| WO | 2005/039303 A2 | 5/2005 |
| WO | 2012082065 A1 | 6/2012 |
| WO | 2013/002783 A1 | 1/2013 |

OTHER PUBLICATIONS

Leach et al. (AAPS PharmSciTech 2005; 6(4):E606-E13 pages).*
Felton et al. (Aqueous Polymeric Coatings for Pharmaceutical Dosage Forms 2008, 3rd Ed. CRC Press pages (in part) 205, 206, 207, 238 and 239).*
Kumar et al. (IJRAPR 2012;2(1):9-19).*
Mohapatra (Liquid Cooling 2006, [online] retrieved from: http://www.electronics-cooling.com/2006/05/an-overview-of-liquid-coolants-for-electronics-cooling/; 4 pages.).*
Kadajji et al. (Polymers 2011;3:1972-2009).*
International Search Report dated Dec. 17, 2013 for PCT/KR2013/002592 and English translation.
Extended European Search Report dated Jul. 11, 2016 which was issued for a related European Application No. 13 880 306.9 (5 pages).

* cited by examiner

METHOD FOR PREPARING ROUND EMULSION BEADS USING LOW TEMPERATURE COOLING AND THE PRODUCT THEREOF

CROSS-REFERENCE TO RELATED APPLICATIONS

This application is a 371 of PCT/KR2013/002592, filed Mar. 28, 2013, the content of which is incorporated herein by reference.

FIELD OF THE INVENTION

The present invention relates to a method for preparing round emulsion beads using low temperature cooling and the product thereof.

BACKGROUND OF THE INVENTION

In recent years, unless products themselves are "remarkable" (differentiated enough to be remembered), they are not sold well. In addition to the excellent performance of a product itself, a "see-tech-marketing" or "Visual Technology Strategy," i.e., sparking visual pleasure from the appearance of the product to attract consumer attention, has been used as a differentiation strategy for cutting through the competition. The color and shape of the product packaging or container as well as the product itself have been specially designed in the cosmetics industry, with the attempt of providing visual pleasure and aesthetic sense when the product is seen or used.

As one of the most typically employed formulation systems in the cosmetics industry, "emulsion" refers to a system where oil phase and water phase are evenly dispersed by emulsion technology. Examples of factors that affect the physical and chemical properties of such emulsion can include the type of surfactant, internal/external phase ratio, emulsion type <oil/water (O/W), water/oil (W/O), water/oil/water (W/O/W) and the like>, thickener, particle size and the like; O/W emulsion normally applied in cosmetics is composed of particles of approximately 0.5-10 µm in size.

Compositions currently used for make-up or skin are generally provided in the form of oil-in-water type emulsions (i.e., excipients constituted of a continuous aqueous dispersion phase and a non-continuous oil dispersion phase) or water-in-oil emulsions (i.e., excipients constituted of a continuous oil dispersion phase and a non-continuous aqueous dispersion phase).

Thus, water-in-oil emulsions contain a continuous oil phase. It allows to prevent the loss of water passing through the epithelium at the surface of the skin and form a lipid membrane that protects the skin from stimulation from the outside. Such emulsions are particularly suitable to protect the skin, supply it with nourishment, and for the treatment of dry skin. Oil-in-water emulsions provide smoother skin, are less oily and give a lighter feeling than when a water-in-oil emulsion is used.

Reflecting the latest trends in cosmetics, i.e., sparking fun and emotion, there have been many attempts to transform the unique form, the color and/or texture of emulsion formulation, so as to provide users with visual pleasure, aesthetic sense and pleasure of make-up in addition to the effects derived when the emulsion cosmetics themselves are used.

In Korea Patent Application No. 10-1995-0012596 (published on 17 Dec. 1996), it is disclosed separately manufacturing aqueous phase (A) containing ethanol and water, and oil phase (B) containing hydrogenated polyisobutene, pearl powder and jojoba oil. The oil phase (B) was completely dispersed in the aqueous phase (A), followed by letting the mixture stand for 30-40 minutes. Then, pearl-colored oil phase beads of 3-8 mm form at the lower portion of the alcohol phase and maintain the shape stably for a long period. External force can destruct the oil phase beads to become micro dispersion in the aqueous phase. After a certain period, they grow to be the pearl-colored oil phase beads of the same size. Therefore, the reversible pearl-colored beads exist as an oil phase itself while the oil phase (B) is not dissolved in the aqueous phase (A). Each bead forms an oil phase particle of o/w emulsion.

Korea Patent Application No. 10-2007-0137515 (published on Jul. 1, 2009) teaches a method for obtaining semi-transparent or translucent polymer gel beads of about 1-2 mm. In order to obtain the beads, a solution of a pigment, carrageenan, agar and polyhydric alcohol is simply cooled to form a gel phase followed by extruding the gel phase through fine nozzles. The beads manufactured through this method do not have any regulated round shape, but are in the form of amorphous soft gel capsule. According to the inventor thereof, the cosmetics containing these beads look like a pomegranate, thereby providing joyous makeup. However, the semi-transparent or translucent polymer gel beads disclosed by the patent application have almost no cosmetic function but merely decorate the appearance of the cosmetics containing the beads.

Korean Patent Application No. 10-2006-004420 (published on Nov. 15, 2007) teaches an emulsion composition containing macro-sized (0.01-5 mm) lipid capsule particles. The lipid capsule particle consists of an outer shell lipid capsule, which is formed with lipid or lipid-like material solid at room temperature, and oil collected therein. In the lipid capsule particles, however, stability improves by providing outer shell lipid to oil phase particles of o/w type emulsion.

As such, beads formulations known are oil phase particles enlarged in o/w emulsion (Korean Patent Application No. 10-1995-0012596), oil phase particles protected by outer shell (Korean Patent Application No. 10-2006-004420), or oil phase itself in a gel that is not dissolved in an aqueous solution and can be destructed by external force (Korean Patent Application No. 10-2007-0137515). It is not disclosed having an emulsion composition itself as beads formulation.

Meanwhile, it was known in the food industry to manufacture bead shape ice cream using a cryogenic freezing method. Ice cream raw material is liquid at room temperature. The ice cream raw material liquid is dropped into a cryogenic refrigerant, such as liquid nitrogen, so as to be solidified in bead shape. The bead shape ice cream manufactured by this method, however, should be stored at a low temperature to maintain the bead shape, as it can revert to be liquid at room temperature.

The present inventors studied and provide a method for manufacturing solid round emulsion beads by applying a low temperature or cryogenic freezing method to liquid emulsion. The present inventors also studied and provide various methods how to maintain the solid round emulsion beads prepared by the same at room temperature.

DESCRIPTION OF THE INVENTION

Problems to Solve

There was a need for not only a method for preparing bead type emulsion, but also a method for maintaining the emulsion in the bead shape for a long period of time at room temperature without swelling and/or disintegration, wherein the bead type emulsion, upon being released from the container and/or being applied on the skin, should easily disintegrate to be applied as a liquid emulsion without any unpleasant foreign substance feeling upon application on the skin.

Tools for Solving the Problems

The present inventors employed a cryogenic method of dropping liquid emulsion into the cryogenic refrigerant for freezing to form solid round emulsion beads. The solid emulsion beads can be stored or used at a low temperature as it is. The solid round emulsion beads can be coated with a solution containing a composition which is solid at room temperature or which can form gel. The emulsion beads can be prepared by using liquid emulsion containing additional composition, which is solid at room temperature or can form gel, in the water phase of oil-in-water (O/W) emulsion or the oil phase of oil-in-water (W/O) emulsion. The emulsion beads can maintain its shape without swelling and/or damage but with stability and does not give any grainy feeling when the liquid emulsion was applied on the skin.

Effect of the Invention

Solid round emulsion beads of the present invention, prepared by a cryogenic freezing method, can be stored and used as it is, at a low temperature. The liquid bead emulsion beads can be obtained using a composition which is solid or can form gel at room temperature. These beads can maintain the shape stably for a long time period without swelling and/or damage at room temperature. When withdrawn from the container or applied on the skin, the beads can be destructed easily to work as a liquid emulsion. The destructed emulsion is applied on the skin without giving unpleasant foreign substance feeling.

DETAILED DESCRIPTION OF THE INVENTION

Figure 1:
FIG. 1 is a photograph of a vessel filled with the white emulsion beads prepared without a pigment as described in Example 3.

The first object of the invention to provide a method for preparing emulsion beads by dropping liquid emulsion to a freezing solvent at a temperature no higher than 0° C. to produce a solid phase emulsion beads.

In the present invention, the above-described freezing refrigerant is refrigerant maintaining low temperature to freeze the liquid emulsion beads to form solid phase emulsion beads. The temperature of coolant (coolant temperature), for example, is at or below 0° C., specifically at a temperature of 0° C.~-200° C., preferably at a temperature of -10° C.~-200° C., more preferably at a temperature of -15° C.~-150° C., specifically it may be selected at a temperature of -20° C.~-100° C. In one embodiment, the low-temperature refrigerant can be selected from the group consisting of: an oil which is liquid at a low temperature such as silicon oil or mineral oil; or liquid gas such as liquid nitrogen, liquid oxygen or liquid air. The oil such as silicon and mineral oils are liquid at a low temperature and can be used as a low temperature refrigerant by using cooler, liquid gas, or other cooling method (for example, a mixture of dry ice and acetone, a mixture of ice and ethanol, etc.) to make it as cold as needed. The liquid gas, such as liquid nitrogen, liquid oxygen, or liquid air gas, can be used as a low temperature refrigerant as it is.

On the other hand, in the present invention the freezing refrigerant is a liquid or liquid mixture having a fluidity in the freezing temperature. The fluidity of the liquid is about 30 centipoise or less at freezing temperature, specifically 20 centipoise or lower, preferably 10 centipoise or less, and more preferably a viscosity of less than 5 centipoise.

Conventional cryogenic refrigerant which may be used as the freezing refrigerant in the present invention can remain in liquid phase at a temperature at or lower than 0° C. and can maintain a temperature at or lower than 0° C. by itself and the example include liquid nitrogen, liquid oxygen or liquid air and also can include liquid hydrocarbons.

In one embodiment of the present invention, the freezing refrigerant is a liquid oil having fluidity at or lower than 0° C., for example, may be a silicone oil and mineral oil. Silicone oils and mineral oils can be preferably used because it can maintain sufficient fluidity in the freezing temperature above because the viscosity does not change by the temperature changes. Examples of silicone oil include dimethyl silicone oil, methylphenyl silicone oil, methyl hydrogen silicone oil, methyl-hydroxy-silicone oil, silicone flow oil, polyoxyethylene ether copolymer, alkyl modified silicone oil, higher fatty acid-modified silicone oil, amino-modified silicone. It can also refer to the oil and the epoxy-modified silicone oil. The mineral oil is a by-product produced in the process referred to as liquid oil, or a mineral oil, obtained during purification of the crude oil, and the main component is an alkane and paraffin.

In general, the cryogenic freezing means freezing at temperature like -200° C. like liquid nitrogen or liquid air, but in the present invention this separation is not critical.

When using an oil in the liquid state at or below 0° C., such as silicone oil or mineral oil, as the refrigerant freezing, freezing temperature is below 0° C., especially from -10° C. or less, preferably -15° C. or less, more preferably -20° C. or less but -100° C. or higher, especially less than -80° C., preferably -60° C. or higher, more preferably be selected -50° C. or higher.

According to one embodiment, the above-mentioned silicone oil and mineral oil is liquid at a low temperature of less than 0° C. as oil cooler, liquefied gas or other cooling techniques (for example, a mixture of dry ice and acetone, ice and ethanol mixture) use can be used as the low temperature coolant to cool to the desired low temperature, and the above-mentioned liquid nitrogen, liquid oxygen, liquid air or liquefied gas, such as may be used by itself as a low-temperature refrigerant. In some cases, it is also possible to use a liquid hydrocarbon with a low temperature refrigerant.

According to one embodiment, the size of the emulsion bead is 0.5-20 mm, preferably 1-10 mm, particularly 2-6 mm.

One embodiment of the method of the present invention may further comprises coating the solid round emulsion bead with a solution containing a lipid composition which is solid at room temperature or a gel-forming composition.

According to one embodiment, the liquid emulsion can be water-in-oil (W/O), oil-in-water (O/W), water-in-oil-in-water (W/O/W), or oil-in-water-in-oil (O/W/O) type emulsion.

According to one preferred embodiment, the liquid emulsion may contain a lipid composition which is continuous phase and solid at room temperature or a gel-forming composition.

According to one embodiment, the lipid composition which is a solid at room temperature can be selected from the group consisting of behenyl alcohol, cetyl alcohol, stearyl alcohol, glyceryl monostearate, cetostearyl alcohol or polyalcohol such as batyl alcohol, fatty acid, lipid peptide and a mixture thereof.

According to one embodiment, the gel-forming composition can be selected from the group consisting of a gel-forming polymer such as a cationic polymer, a gum composition such as Indiana gum, guar gum or Traganth gum, carrageenan, agar, and a mixture thereof.

The second object of the invention is providing solid phase emulsion beads obtained by a method for preparing emulsion beads comprising dropping liquid emulsion to a low temperature refrigerant liquid.

According to one variant of the invention, the emulsion bead can also be an angulated shape, rod shape, cylindrical shape, rugby ball shape, or chain shape.

In the present invention, the droplet size (diameter or longest distance) of the emulsion is 0.5-20 mm, specifically, 1-10 mm, and preferably 2-8 mm, especially from 3-6 mm. The droplet of the emulsion can be controlled by modifying the emulsion viscosity, the nozzle diameter, or the spray pressure. A person of ordinary skill in the art can adjust the emulsion viscosity, the nozzle diameter, or the spray pressure to obtain desirably sized droplet.

In the present invention, the solution (hereafter "coating solution") used for coating the solid round emulsion beads can contain a lipid composition solid at room temperature or a gel-forming composition. The coating solution can be dispersed liquid or may have be in emulsion form. The coating can be performed by spraying the coating solution, or dipping in the coating solution, or by rolling on a film of the coating solution. The temperature of coating process or coating solution is not limited specifically, but any temperature is allowable as long as the solid round emulsion beads do not dissolve during the coating process. For example, the coating temperature can be no higher than 0° C., preferably no higher than −10° C., more preferably no higher than −20° C. The coating solution can be at the temperature similar to the process temperature or at 5-10° C. lower than the process temperature. Preferably, it would be beneficial to consistently coating and adjusting coating thickness, if the coating solution remains liquid during the process or at the process temperature.

For example, the round emulsion beads of the present invention can be prepared by use of an oil-in-water (O/W) type emulsion, as follows. The coating solution is prepared by dissolving or dispersing lipid composition, which is solid at room temperature (for example, behenyl alcohol or glyceryl monostearate), in ethanol, and cooling it to −10° C. The coating solution is sprayed to the solid round emulsion beads, and ethanol is removed under reduced pressure to form a film on the surface of the solid round emulsion beads. Then, the temperature is increased to reach room temperature. The liquid emulsion is collected within the lipid film and obtain it as round beads. The lipid composition solid at room temperature is included in about 0.1-10 wt %, specifically 0.2-7 wt %, preferably 0.3-5 wt %, more preferably 0.5-5 wt % of the total weight of the solid round emulsion beads. When the amount of the lipid composition is no more than 0.1 wt %, it may be difficult to maintain the shapes of the resultant round emulsion beads at room temperature. If it is no less than 10 wt %, the round emulsion beads cannot be easily cracked, or grainy feelings may increase when applied on the skin.

In the present invention, the gel-forming material is selected from a group consisting of a gel-forming polymer, such as a cationic polymer; a gum material, such as Indian gum or guar gum; carrageenan; agar and a mixture thereof. In addition, plant extract such as Tragacanth gum or Arabian gum; plant materials such as locust bean gum seed gum, guar gum, and; semi-synthetic rubber-like material, such as CMC (carboxymethyl cellulose), hydroxypropyl cellulose and methyl cellulose; seaweed extract such as alginate; fermentation products such as Xanthan gum and dextran; and low methoxy pectin. The gel-forming material is included in the round emulsion beads in 0.1 to 5% by weight, especially from 0.2 to 4% by weight, preferably 0.4 to 3% by weight, more preferably from 0.5 to 2% by weight of the total weight of the beads. If the amount is no more than 0.1 wt %, it is difficult to maintain the shapes of the resultant round emulsion beads at room temperature. If it is no less than 5 wt %, the round emulsion beads cannot be easily cracked, or grainy feelings may increase when applied on the skin.

According to a particular embodiment of the present invention, a single bead where two different emulsions co-exist can be produced by making emulsions having a same or different compositions as a liquid droplet, and dropping and freezing the liquid droplet at a low temperature. The method for preparing the liquid droplet with two or more emulsions is not limited. For example, it can be prepared using Y-shape type tip, which has two or more branches for supply of raw material within a single nozzle, or a hollow type tip having the supply branch in another supply branch. The ratio of the emulsion feeding can be controlled by modifying the diameter of the supply branch for the Y-shape type tip or the hollow type tip, the speed of the raw material feeding, and/or the diameter of the nozzle tip.

According to another particular embodiment of the present invention, it is also possible to prepare the round emulsion beads having emulsions layered with the same core, wherein the multiple emulsions can have a same or different compositions. First, one emulsion is used to produce solid round emulsion beads by a low-temperature freezing method, and additional emulsion is either sprayed or coated on top of the beads and they are treated with a low-temperature freezing process to provide multi-layered round emulsion beads. Or, the hollow tip can be used for the liquid droplets to control the emulsion feeding speed to provide the multi-layered liquid droplets. Alternatively, it is also possible to use any method for producing liquid droplets with a core-shell structure.

According to the method, each bead can contain two or more layered emulsions having different functions (e.g., color, fragrance), or compositions (different compositions, different ratios). The method for preparing the round emulsion beads having two or more layered emulsions having different functions, for example, can be used for preparing cosmetic compositions using color transferring system.

On the other hand, the present invention can prepare a round bead-form emulsion or an emulsion having a round bead form from any emulsion having water phase as the continuous phase, including O/W emulsion. Up to now, making the emulsion itself in a round bead shape or impregnated in the form of capsules, i.e., the beads or the capsules containing emulsion as it is were not known, and thus, the present invention provides new fields and application potential in cosmetic formulation industry.

In addition, in the bead shape products such as STARPHERE (a marketed product by KTP) and Unisphere products (a marketed product by INDU Chem), cosmetic raw material for Visual Carrier System is provided in bead shape. However, they do not swell in oil phase and thus, can be used only in cosmetics having water continuous phase, such as O/W emulsion.

On the other hand, because the round emulsion beads of the present invention are already swollen and can deliver the unique emulsion feeling for application, they can offer very distinct and superior application feeling compared to the conventional simple shaped arginic acid beads of agar beads. In addition, the emulsion beads of the present invention can be utilized for compositions having oily continuous phase (e.g. W/O emulsion) or water continuous phase (e.g. O/W emulsion).

The present invention is described below in more details by the following examples.

Example 1

(1) Preparation of Water in Oil Emulsion

A water in oil emulsion was prepared based on the compositions in Table 1 by the steps of (a) to (d). The composition of each ingredient in Table 1 is weight %.

TABLE 1

| | | Example 1 |
|---|---|---|
| Oil Phase | Stearyl alcohol | 2.20 |
| | Stearic acid | 1.00 |
| | Glyceryl stearate | 2.00 |
| | Mineral oil | 30.00 |
| Water Phase 1 | Purified water | To 100 |
| | Disodium EDTA | 0.02 |
| | Triethanolamine | 0.2 |
| | Propylene glycol | 3.00 |
| Water Phase 2 | Purified Water | 10 |
| | Carbomer | 0.05 |

(a) All ingredients for the Oil Phase in Table 1 were mixed evenly with heating (70-75° C.).
(b) All ingredients for the Water Phase 1 in Table 1 were dissolved and mixed evenly with heating (70-75° C.).
(c) The mixture of (a) was added to the solution (b) at the temperature of 70-75° C. with stirring to obtain an emulsion.
(d) The Water Phase 2 was added to increase the viscosity and cooled to about 30° C.

(2) Preparation of Solid Round Emulsion Beads

Mineral Oil is cooled to −78° C. using dry ice and acetone. The water-in-oil liquid emulsion obtained from (1) was dropped through tip of 1 mm diameter to the mineral oil, so as to form a liquid droplet having diameter of 2-3 mm. The round emulsion beads are isolated and stored in a refrigerator at −10° C. Even after storing a long time period, no change in shape or aggregation was observed.

Example 2

(1) Preparation of Water-in-Oil Emulsion

Except adding 1 wt % of carrageenan to the Water Phase 1, the same procedure was used as described in Example 1 to form water-in-oil emulsion.

(2) Preparation of Solid Round Emulsion Beads

Except that the mineral oil is cooled to −20° C. in a low temperature refrigeration circulator, the same procedure described in Example 1 was used to prepare solid round emulsion beads.

(3) Preparation of the Cosmetic Raw Material Comprising Round Emulsion Beads

The solid round emulsion beads obtained from (2) were filled into a clear container. Thereto was added a mineral oil, and the resulting mixture was warmed up to room temperature to convert the round emulsion beads to liquid phase.

Although the liquid round emulsion beads in a clear container were allowed to stand for a long period time at room temperature, no damage by swelling, aggregation, or compression, or no change in shape was observed in the beads. There was no change in the transparency and/or color in the medium observed.

(4) Use of the Cosmetic Raw Material Containing Round Emulsion Beads

A sprayer was installed on the clear container filled with the liquid round emulsion beads. Pressing the sprayer broke the liquid emulsion beads around the injecting tube and the liquid emulsion was ejected through the outlet of the sprayer.

Example 3

(1) Preparation of Water-in-Oil Emulsion

According to the composition shown in Table 2, the ingredients in the Water Phase 1 (Raw Material 3) were mixed, heated to 90° C. and dissolved to make the Water Phase 1. The resultant Water Phase 1 was delivered to a main mixer.

Next, according to the composition shown in Table 2, ingredients for the Oil Phase (Raw Material 1) were mixed and heated to 72-74° C. to prepare an oil phase. To the oil phase, Silicon 244 (Raw Material 2) was added at 68-70° C. and the resultant mixture was delivered to the main mixer.

The Raw Material 1, 2 and 3 were emulsified.

In a gum mixer, a thickening agent (e.g. carbopol 941) (Raw Material 5) was dispersed in purified water (Raw Material 4) to prepare the Water Phase 2. The Water Phase 2 was delivered to the main mixer and emulsified again.

When the temperature of the produced emulsion is reduced to 48-50° C., a solution of preservatives (e.g. GERMALL 115), MPC (milk protein concentrates), and Fragrance (components 6-8) dissolved in a small amount of water was added to the main mixer and the mixture was heated to about 70° C. The product emulsion was prepared at the temperature.

(2) Preparation of Solid Round Emulsion Beads

The obtained emulsion was dropped into mineral oil at −20° C. through a nozzle tip and isolated upon freezing to obtain solid round emulsion beads with milk white color, i.e. characteristic color of an emulsion. The obtained solid round emulsion beads have about 2-3 mm size and composition of Table 2. FIG. 1 shows the product obtained in Example 3.

TABLE 2

| Phase | Raw Material | Ingredients or Commercial Product name | Content (Wt %) |
|---|---|---|---|
| Oil Phase | 1 | Lanetto-O | 0.67 |
| | | Arlacel-165 | 0.84 |
| | | W4kEM-205 | 1.01 |
| | | Prophyl Paraben | 0.06 |

TABLE 2-continued

| Phase | Raw Material | Ingredients or Commercial Product name | Content (Wt %) |
|---|---|---|---|
| | | Isocetylmyristate (ICM-R) | 5.04 |
| | | Octyldodecyl myristate (EUTANOL GM) | 1.68 |
| | | Emusifier (TEGO CARE PS) | 1.26 |
| | 2 | Silicon 244 (SILICONE 244) | 0.84 |
| Water Phase 1 | 3 | Purified water | 55.94 |
| | | P.G | 2.52 |
| | | Glycerin (98%_) | 3.36 |
| | | Preservative (DANISOL-M) | 0.17 |
| | | Disodium EDTA | 0.02 |
| | | Agar | 1.00 |
| | | TEA-PURE | 0.10 |
| Water Phase 2 | 4 | Purified Water | 10.08 |
| | 5 | Emulsifier (CARBOPOL 941) | 0.10 |
| Excipients | 6 | Preservative (GERMALL 115) | 0.17 |
| | 7 | MPC | 0.02 |
| | 8 | Fragrance | 0.13 |

The shape change or breakage was not observed even after the solid round emulsion beads were converted to liquid at room temperature. The obtained round emulsion beads can be used as liquid emulsion by applying on the skin and rubbing. Upon application, all ingredients in the emulsion beads did not leave any grainy feeling or leaving any residue and provide the same or similar touch and utility feeling from those emulsions prepared without these ingredients.

Example 4

Except that different pigments (single or mixture) were added to the Water Phase 1, the process of Example 3 was repeated to prepare round emulsion beads with different colors except milk white. The obtained round emulsion beads were about 2-3 mm size.

Example 5

Figure 2:
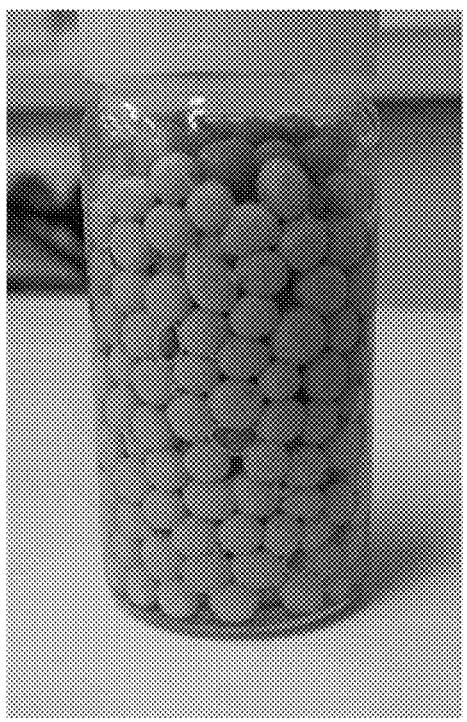
FIG. 2 is a photograph of a vessel filled with the emulsion beads prepared with a pigment as described in Example 4.

Except that a variety of pearl was added to the Water Phase 1, the process of Example 3 was repeated to prepare round emulsion beads with pearl color. The obtained round emulsion beads were about 2-3 mm size. FIG. 2 shows the obtained product from Example 5.

Example 6

Using a similar procedure as described in Example 3, the milk white Water Phase 1a and the Water Phase 1b prepared by adding green pigments were fed through the Y-shaped nozzle tip (top has two nozzle tip which are combined downfall to form a single tip at the end) simultaneously to drop to form round emulsion beads having two colors.

Figure 3:
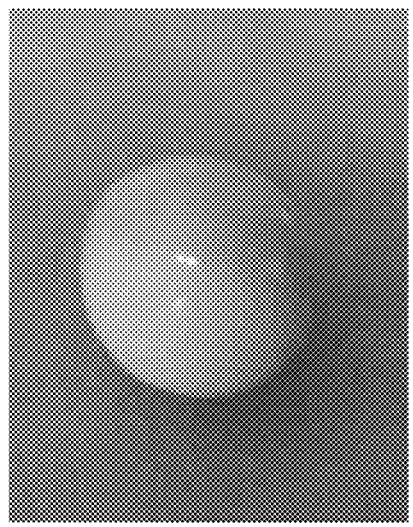
FIG. 3 is a photograph of the emulsion beads having two colors, prepared as described in Example 6.

The obtained two colored round emulsion beads were about 2-3 mm size. FIG. 3 shows the obtained product from Example 6 as magnified 10 times.

Test Example

The round emulsion beads prepared from Examples 4-6 were filled into the spray equipped container. No other external pressure or force was added to allow the round emulsion beads to be filled naturally by gravity.

Even though the round emulsion beads were thawed from solid to liquid while they were stored at room temperature, the beads maintained its bead shape without swelling, changes of shape or color, or damage. In addition, not only the emulsion beads maintained the bead shape without swelling, changes of shape or color, or damage after a long period storage, but also the medium where the beads were stored did not change color due to leaking or diffusion.

In the discharge test with a sprayer, the liquid round emulsion beads in the container were drawn into the spray tubing without any resistance and it was also observed that consistent emulsion was released as liquid through the releasing outlet.

Also by applying a liquid emulsion discharged on the skin, the component used to form the bead shape did not leave any residue on the skin or leave any grainy feeling, and gave an emulsion with the same or a similar texture and feeling prepared without these ingredients.

INDUSTRIAL UTILITY

The invention can be used in the cosmetic industry.

The invention claimed is:

1. A method for preparing a round emulsion bead comprising:
dropping liquid emulsion to a cryogenic refrigerant at a temperature of no higher than 0° C. to prepare a solid round emulsion bead of about 0.5-20 mm in diameter, wherein the liquid emulsion comprises a lipid composition which is solid at room temperature;
wherein the cryogenic refrigerant is silicone oil or mineral oil; and
warming said solid round emulsion bead to room temperature to prepare a liquid round emulsion bead having the same shape and size as said solid round emulsion bead.

2. The method of claim 1, wherein the cryogenic refrigerant is at −10 to −200° C.

3. The method of claim 1, wherein the liquid emulsion is water-in-oil (W/O), oil-in-water (O/W), water-in-oil-in-water (W/O/W), or oil-in water-in-oil (O/W/O) type emulsion.

4. The method of claim 1, further comprising coating the solid round emulsion bead with a solution comprising a lipid composition which is solid at room temperature.

5. The method of claim 4, wherein the lipid composition which is solid at room temperature is selected from the group consisting of behenyl alcohol, cetyl alcohol, stearyl alcohol, glyceryl monostearate, cetostearyl alcohol, poly alcohols, fatty acid, lipid, peptides and a mixture thereof.

6. The method of claim 1, comprising preparing a liquid droplet by mixing two or more liquid emulsions and dropping the liquid droplet to form a round emulsion bead.

7. The method of claim 1, wherein two or more different liquid emulsions are combined using a Y-shaped or hollow-shaped tip to form a liquid droplet.

* * * * *